United States Patent
Gainer

(10) Patent No.: US 8,206,751 B2
(45) Date of Patent: Jun. 26, 2012

(54) CLASS OF THERAPEUTICS THAT ENHANCE SMALL MOLECULE DIFFUSION

(75) Inventor: John L. Gainer, Charlottesville, VA (US)

(73) Assignee: Diffusion Pharmaceuticals LLC, Charlottesville, VA (US)

( * ) Notice: Subject to any disclaimer, the term of this patent is extended or adjusted under 35 U.S.C. 154(b) by 355 days.

(21) Appl. No.: 12/289,713

(22) Filed: Oct. 31, 2008

(65) Prior Publication Data

US 2009/0110746 A1 Apr. 30, 2009

Related U.S. Application Data

(60) Provisional application No. 61/001,095, filed on Oct. 31, 2007.

(51) Int. Cl.
*A61K 33/42* (2006.01)

(52) U.S. Cl. .......... 424/601; 514/53; 514/423; 514/547; 514/551

(58) Field of Classification Search ................... 424/601; 514/53, 423, 547, 551
See application file for complete search history.

(56) References Cited

U.S. PATENT DOCUMENTS

| | | |
|---|---|---|
| 2,175,843 A | 10/1939 | Kuhn et al. |
| 2,948,748 A | 8/1960 | Guex et al. |
| 3,489,806 A | 1/1970 | Gutmann et al. |
| 3,687,990 A | 8/1972 | Gutmann et al. |
| 3,788,468 A | 1/1974 | Gainer |
| 3,853,993 A | 12/1974 | Gainer et al. |
| 3,965,261 A | 6/1976 | Gainer |
| 3,975,519 A | 8/1976 | Gainer |
| 4,009,270 A | 2/1977 | Gainer, Jr. |
| 4,038,144 A | 7/1977 | Gainer |
| 4,046,880 A | 9/1977 | Gainer |
| 4,070,460 A | 1/1978 | Gainer, Jr. |
| 4,099,270 A | 7/1978 | Jabour |
| 4,105,855 A | 8/1978 | Schulz et al. |
| 4,176,179 A | 11/1979 | Gainer |
| 4,216,211 A | 8/1980 | Francis |
| 4,699,664 A | 10/1987 | Hettiarachchy et al. |
| 5,053,240 A | 10/1991 | Todd, Jr. |
| 5,107,030 A | 4/1992 | Babler |
| 5,424,407 A | 6/1995 | Tanaka et al. |
| 5,472,946 A | 12/1995 | Peck et al. |
| 5,811,119 A | 9/1998 | Mehta et al. |
| 5,817,332 A | 10/1998 | Urtti et al. |
| 6,060,511 A | 5/2000 | Gainer |
| 6,150,561 A | 11/2000 | Kreienbuhl et al. |
| 7,145,025 B2 | 12/2006 | Lockwood et al. |
| 7,446,101 B1 | 11/2008 | Madhavi et al. |

(Continued)

FOREIGN PATENT DOCUMENTS

CH 522 572 6/1972

(Continued)

OTHER PUBLICATIONS

EPO Office Action dated Nov. 9, 2009 in applicant's European application corresponding to PCT/US03/26424.

(Continued)

*Primary Examiner* — Deborah D Carr
(74) *Attorney, Agent, or Firm* — Nixon & Vanderhye P.C.

(57) ABSTRACT

The subject invention relates to novel compositions containing a diffusion enhancing compound and their use in treating a variety of disorders.

3 Claims, 4 Drawing Sheets

U.S. PATENT DOCUMENTS

| | | |
|---|---|---|
| 2002/0055486 A1 | 5/2002 | Matsuo et al. |
| 2003/0180282 A1 | 9/2003 | Serebruany et al. |
| 2003/0186931 A1 | 10/2003 | Matsuo et al. |
| 2004/0109920 A1 | 6/2004 | Reuscher et al. |
| 2004/0116729 A1 | 6/2004 | Gainer et al. |
| 2006/0194973 A1* | 8/2006 | Gainer et al. .............. 554/121 |
| 2006/0276372 A1 | 12/2006 | Lockwood et al. |
| 2007/0088248 A1 | 4/2007 | Glenn et al. |
| 2008/0113031 A1 | 5/2008 | Moodley et al. |
| 2008/0255246 A1 | 10/2008 | Gainer |
| 2009/0110746 A1 | 4/2009 | Gainer |
| 2009/0169586 A1 | 7/2009 | Tracton |
| 2009/0176287 A1 | 7/2009 | Schmidt-Dannert et al. |

FOREIGN PATENT DOCUMENTS

| | | |
|---|---|---|
| EP | 0 908 449 | 4/1999 |
| EP | 0 908 449 A1 | 4/1999 |
| EP | 0908449 A1 | 4/1999 |
| EP | 1192947 A1 | 4/2002 |
| JP | 45-14114 | 5/1970 |
| JP | 45-014114 | 5/1970 |
| JP | 61-254161 | 11/1986 |
| JP | 63-059831 | 3/1988 |
| JP | 63-59831 | 3/1988 |
| JP | 63059831 | 3/1988 |
| JP | A 03-056412 | 3/1991 |
| JP | A 04-264020 | 9/1992 |
| JP | 05-032531 | 2/1993 |
| JP | 05032531 | 2/1993 |
| JP | A 05-178765 | 7/1993 |
| JP | 06-248193 | 9/1994 |
| JP | 07-023736 | 1/1995 |
| JP | 7-223960 | 8/1995 |
| JP | A 07/291854 | 11/1995 |
| JP | 10-502388 | 3/1998 |
| JP | 11-180901 | 6/1999 |
| JP | 11-209642 | 8/1999 |
| JP | 2002-524535 | 8/2002 |
| JP | A 03-26607 | 1/2003 |
| KR | 1999-0036861 | 5/1999 |
| WO | WO 92/15544 | 9/1992 |
| WO | WO 9215544 | 9/1992 |
| WO | WO 95/00130 | 1/1995 |
| WO | WO 9500130 | 1/1995 |
| WO | WO 98/14183 | 4/1998 |
| WO | WO 98/14183 A1 | 4/1998 |
| WO | WO 9814183 | 4/1998 |
| WO | WO 9814183 A1 | 4/1998 |
| WO | WO 99/15150 | 4/1999 |
| WO | WO00/15262 | 3/2000 |
| WO | WO 03/072734 | 9/2003 |
| WO | WO 03/072734 A2 | 9/2003 |
| WO | WO 03072734 | 9/2003 |
| WO | WO 2004/048323 | 6/2004 |
| WO | WO 2004/049095 | 6/2004 |
| WO | WO 2004/049095 A2 | 6/2004 |
| WO | WO 2004/049095 A3 | 6/2004 |
| WO | WO 2004049095 | 6/2004 |
| WO | WO 2005/028411 | 3/2005 |
| WO | WO 2005/028411 A1 | 3/2005 |
| WO | WO 2005/120495 | 12/2005 |
| WO | WO 2005120495 | 12/2005 |
| WO | WO 2006/039685 | 4/2006 |
| WO | WO 2006/104610 | 10/2006 |
| WO | WO 2006/104610 A2 | 10/2006 |
| WO | WO 2007/072529 | 6/2007 |

OTHER PUBLICATIONS

Wirz, R., et al, *Helv.Chim.Acta*, vol. 43, No. 6, 1960, pp. 1738-1745 (XP008042762).
Isler, O., et al, *Helv. Chim. Acta*, vol. 40, No. 5, 1957, pp. 1242-1249 (XP008042920).
Database Caplus Chemical Abstracts Service, Columbus, Ohio (XP002317165).
Wenkert, E., et al, *J. Org. Chem.*, vol. 55, No. 25, 1990, pp. 6203-6214 (XP002317164).
Database Caplus Chemical Abstracts Service, Columbus, Ohio (XP002317166).
Gibson, T.W., et al, *J. Org. Chem.*, vol. 41, No. 5, 1976, pp. 791-793 (XP002325593).
Ladig, K.E., et al, JACS, vol. 120, No. 36, 1998, pp. 9394-9395 (XP 002970835).
EPO Office Action dated Nov. 9, 2009 in applicant's European application corresponding to PCT/US03/05521.
Wenkert, E., et al, *J. Org. Chem.*, vol. 55, No. 25, 1990, pp. 6203-6214.
Korean Office Action dated Nov. 23, 2009 in applicant's corresponding Korean application No. 10-2006-7003827.
Pure & Appl. Chem., vol. 69, No. 10, pp. 2047-2060, 1997, "Carotenoid synthesis: A progress report."
Examination Report dated Oct. 6, 2008 issued by the New Zealand Patent Office in one of Applicants' corresponding foreign applications.
India Office Action dated Oct. 23, 2008 in a corresponding application owned by the applicants (India Patent App No. 676/DELNP/2006).
Chinese Office Action dated Nov. 7, 2008 in a corresponding application owned by the applicants (Chinese App No. 03826969.4).
Laidig, K.E. et al, Altering Diffusivity in Biological Solutions through Modification of Solution Structure and Dynamics, *Journal of the American Chemical Society*, 1998, vol. 120, No. 36, pp. 9394-9395.
Japanese Office Action and its English Translation dated Jan. 12, 2010 in the Assignee's Japanese application relating to PCT/US 03/26424.
Supplementary European Search Report dated Dec. 8, 2010 (corresponding to applicant's European Regional Phase Patent Application No. EP 08844993.9 based on International Patent Application No. PCT/US2008/012440 filed on Oct. 31, 2008).
Chinese Patent Office—Third Office Action in Chinese Patent Application No. 03804566.4 dated Jan. 23, 2009.
New Zealand Office Action dated Jan. 21, 2011.
Johnson et al, *Journal of Pharmaceutical Science*, vol. 85, No. 7, 1996, pp. 670-679, "Synergistic effects of chemical enhancers and therapeutic ultrasound on transdermal drug delivery."
International Searching Authority Invitation dated Jan. 13, 2009 in PCT/US 08/12440.
Johnson, Mark E, et al, *Journal of Pharmaceutical Sciences*, vol. 85, No. 7, Jul. 1996, pp. 670-679, entitled "Synergistic Effects of Chemical Enhancers and Therapeutic Ultrasound on Transdermal Drug Delivery."
Holloway, G.M., et al, The American Physiological Society, 1988, pp. 683-686—Department of Chemical Engineering, and Dept. of Anesthesiology, School of Medicine, Univ. of VA, Charlotteville, Va; "The carotenoid crocetin enhances pulmonary oxygenation."
Okonkwo, D.O., et al, Neuroscience Letters 352 (2003) 97-100, "Trans-sodium crocetinate increases oxygen delivery to brain parenchyma in rats on oxygen supplementation."
Seyde, Walter C., et al, Journal of Cerebral Blood Flow and Metabolism, vol. 6, No. 6, 1986, pp. 703-707, "Carotenoid Compound Crocetin Improves Cerebral Oxygenation in Hemorrhaged Rats."
Chinese Office Action and its English Translation dated Feb. 12, 2010 in the Assignee's Chinese application relating to PCT/US 06/06422.
Chinese Office Action and its English Translation dated Feb. 21, 2011 in the Assignee's Chinese application relating to PCT/US 06/06422.
PCT Notification dated Mar. 25, 2009 in PCT/US 08/12440.
International Search Report dated Mar. 25, 2009 in PCT/US 08/12440.
Written Opinion dated Mar. 25, 2009 in PCT/US 08/12440.
Johnson, M.E., et al, *Journal of Pharmaceutical Sciences*, vol. 85, No. 7, pp. 670-679, Jul. 1996, "Synergistic effects of chemical enhancers and therapeutic ultrasound on transdermal drug delivery."
Mexican Office Action dated Feb. 23, 2009 in a corresponding application owned by the applicants (Mexican Patent App No. PA/a/2004/008253).
U.S. Appl. No. 10/647,132, filed Aug. 2003, Gainer.
U.S. Appl. No. 11/361,054, filed Feb. 2006, Gainer.
International Search Report and Written Opinion mailed Jul. 22, 2008.

Office Action dated Jun. 25, 2008 from corresponding Australian Patent Office.
Examination Report dated Jan. 8, 2008 from corresponding New Zealand Patent Office.
Database Caplus, Chemical Abstracts Service, Columbus, Ohio, US; XP002317165 [Japan 63 059831].
Database Caplus, Chemical Abstracts Service, Columbus, Ohio, US; XP002317166 [Japan 05 032531].
Gainer, J.L., et al, *Atherosclerosis*, 19: 135-138, 1974, "Oxygen diffusion and atherosclerosis."
Craw, M., et al, *Photochemitry and Photobiology*, vol. 38 (2), 241-243 (1983).
International Search Report Dec. 24, 2003.
Supplementary Partial European Search Report—Feb. 25, 2005.
Supplementary Partial European Search Report—Apr. 21, 2005.
International Search Report and Written Opinion mailed Oct. 19, 2006 in PCT/US06/06422.
Database HCAPLUS on STN, DN 141:388250, Magesh, V. "Studies on the anti-tumor effect of crocetin against benzo(a)pyrene induced lung cancer in Swiss albino mice." Biomedicine, (CHennai, India) (2003), 23 (3 & 4), 96-99, Abstract.
R. Wirz et al, Helv. Chim. Acta, vol. 43, No. 6, 1738-1745 (1960), XP008042762.
O. Isler et al, Helv. Chim. Acta, vol. 40, No. 5, 1242-1249 (1957), XP008042920.
E. Wenkert et al, J. Org. Chem., vol. 55, No. 25, 6203-6214 (1990); XP-002317164.
T.W. Gibson et al, J. Org. Chem., vol. 41, No. 5, 791-793 (1976); XP-002325593.
Coppola, G.M., Syn. Communications 1021 (Dec. 1984).
Office Action dated Sep. 28, 2007 from U.S. Appl. No. 11/723,383.
International Preliminary Examination Report dated May 25, 2007.
*Carotenoids* vol. 1A: Isolation and Analysis, Edited by G. Britton, S. Liaaen-Jensen and H. Pfander, Birkhauser Verlag, Basel, 1995, pp. 103-107; p. 283.
Roy, et al, *Shock*, vol. 10, No. 3, pp. 213-217 (1998).
Singer et al, *Crit Care Med*, vol. 28, No. 6, pp. 1968-1972 (2000) Intravenous crocetinate prolongs survival in a rat model of lethal hypoxemia.
Wurtman, R.J., *Scientific American*, vol. 252, 1985 Alzheimer's Disease.
Kalani, M., et al, *Journal of Diabetes & Its Complications*, vol. 16, No. 2, pp. 153-158 (2002).
Denninghoff et al, *Diabetes Technology & Therapeutics*, vol. 2, No. 1, pp. 111-113 (2000).
Buchta and Andree, *Naturwiss*, The Total Synthesis of trans-2,2-Bisdimethyl-crocetin-dimetyl ester and trans-Crocetin-dimethyl ester, (1959).
Jansen, F.J.H.M., et al, *Recl. Trav. Chem. Pays-Bas*, 113, 552 (1994).
Gree, R., et al, *Tetrahedron Letters*, 27, 4983 (1986).
Letham, D.S., et al *Phytochemistry* 10, 2077 (1971).
Buchta, E. and Andree, F., *Chem. Ber.* 93, 1349 (1960).
Snyder, J.M., et al, *J. Am. Oil Chem. Soc.*, 59, 469 (1982).
U.S. Appl. No. 60/907,718, filed Apr. 2007, Gainer.
Moelbert, S., et al, *Biophuysical Chemistry* 112, 45-57, 2004 "Kosmotropes and chaotropes: modeling preferential exclusion, binding and aggregate stability."
Gainer, J.L., et al, *Chem. Eng. Commun.*, 15, pp. 323-329, 1982 "Using Excess Volume of Mixing to Correlate Diffusivities in Liquids."
Gainer, J.L., *Ind. Engr. Chem. Research*, vol. 33, pp. 2341-2344, 1994 "Altering Diffusivities in Dilute Polymeric and Biological Solutions."
Okonkwo, D.O., et al, *Neuroscience Letters*, 352, pp. 97-100, 2003, "Trans-sodium crocetinate increases oxygen delivery to brain parenchyma in rats on oxygen supplementation."
Giassi, L.J., et al, *Journal of Trauma*, 51:932-938, 2001, "Trans Sodium Crocetinate Restores Blood Pressure, Heart Rate, and Plasma Lactate after Hemorrhagic Shock."
Gainer, J.L., et al, *Pulmonary Pharmacology & Therapeutics*, 18, pp. 213-216, 2005, "The effect of trans sodium crocetinate (TSC) in a rat oleic acid model of acute lung injury."

Holland, R.A.B., et al, *Respiration Physiology*, 59, pp. 71-91, 1985, "Kinetics of O2 Uptake and Release by Red Cells in Stopped-Flow Apparatus: Effects of unstirred Layer."
Huxley, V.H., et al, *J. Physiol.*, 316, pp. 75-83, 1981, "The Effect of the Red Cell Membrane and a Diffusion Boundary Layer on the Rate of Oxygen Uptake by Human Erythrocytes."
Yamaguchi, K., et al, *J. Applied Physiology*, 58: 1215-1224, 1985.
Laidig, K. E., et al, *Journal of the American Chemical Society*, vol. 120, No. 36, pp. 9394-9395, 1998, "Altering Diffusivity in Biological Solutions through Modification of Solution Structure and Dynamics."
Stennett, A.K., et al, *J. Phys. Chem. B.*, vol. 110, No. 37, pp. 18078-18080, 2006, "trans-Sodium Crocetinate and Diffusion Enhancement."
Secor, R.M., *A.I.Ch.E. Journal*, vol. 11, No. 3, pp. 452-456, 1965, "The Effect of Concentration on Diffusion Coefficient in Polymer Solutions."
*CRC Handbook of Chemistry and Physics*, edited by D.R. Lide, PH.D., CRC Press, Boca Raton, FL, 6-181, 1998.
Goldstick, T.K., PhD Dissertation, University of California, Berkeley, CA, pp. 13-28, 1996, "Diffusion of Oxygen in Protein Solutions."
Ahmad, A.S., et al, *Pharmacology Biochemistry and Behavior*, 81 (2005) pp. 805-813, "Neuroprotection by cretin in a hemiparkinsonian rat model."
Chinese Patent Office Action dated Apr. 6, 2011, from Chinese Patent Application No. 200680013663.0 based on PCT/US2006/06422, and its English translation.
Ladig et al, *J. Am. Chem. Soc.*, 120, 9394-9395 (1998).
Chinese Patent Office Action dated Apr. 6, 2011, and English translation.
Examination Report dated Apr. 7, 2010 issued by the New Zealand Patent Office in Applicants' corresponding foreign application No. 584433.
Isler, O., et al, Helv. Chim. Acta, vol. 40, No. 5, 1957, pp. 1242-1249, (XP008042920).
Database Caplus, Chemical Abstracts Service, Columbus, Ohio, US; (XP002317165) [JP 63 059831].
Wenkert, E., et al, J. Org. Chem., vol. 55, No. 25, 1990, p. 6203-6214 (XP002317164).
Database Caplus, Chemical Abstracts Service, Columbus, Ohio, US; (XP002317166) [JP 05 032531].
Gibson, T.W., et al, J. Org. Chem., vol. 41, No. 5, 1976, pp. 791-793, (XP002325593).
Polish Office Action dated Feb. 23, 2010 from Polish Patent Application No. P-373780 based on PCT/US03/05521.
Chinese Office Action dated Mar. 29, 2010 from Chinese Patent Application No. 03826969.4 based on PCT/US03/26424.
U.S. Appl. No. 60/907,718, filed Feb. 2007, Gainer.
U.S. Appl. No. 61/001,095, filed Oct. 2007, Gainer.
Cutright, D.E., et al, *Radiation Research*, 48, pp. 402-408 (1971) "Long-Term Effects of Radiation on the Vascularity of Rat Bone—Quantitative Measurements with a New Technique."
White, D.C., MD, *Cancer*, 37, pp. 1126-1143, February Supplement (1976), "The Histopathologic basis for functional decrements in late radiation injury in diverse organs."
Marx, R.E., DDS, *J. Oral Maxillofac Surg*, 41, pp. 283-288, (1983), "Osteoradionecrosis: A New Concept of its Pathophysiology."
Calvo, W., et al, *The British Journal of Radiology*, 61, pp. 1043-1052, (1988), "Time- and dose-related changes in the white matter of the rat brain after single doses of X rays."
Kamiryo, T., et al, *Acta Neurochir (Wien)*, 138, pp. 451-459, (1996), "Histological Changes in the Normal Rat Brain After Gamma Irradiation."
Kamiro, T., et al, *Neurosurgery*, vol. 49, No. 2, pp. 409-415, Aug. 2001, "Radiosurgery-induced Microvascular Alterations Precede Necrosis of the Brain Neuropil."
Miyagawa, H., et al, *Neuropathology*, 16, pp. 126-132, (1996), "Pathogenesis of delayed radiation injury in the rat spinal cord after X-ray irradiation."
Okeda, R., *Neuropathology*, 23, pp. 153-160, (2003), "Pathological changes in the cerebral medullary arteries of five autopsy cases of malignant nephrosclerosis: Observation by morphometry and reconstruction of serial sections."

Lyubimova, N., et al, *The British Journal of Radiology*, 77, pp. 488-492, (2004), "Experimental evidence to support the hypothesis that damage to vascular endothelium plays the primary role in the development of late radiation-induced CNS injury."

Bui, Q-C, et al, *Int. J. Radiation Oncology Biol. Phys.*, vol. 60, No. 3, pp. 871-878, (2004), "The Efficacy of Hyperbaric Oxygen Therapy in the Treatment of Radiation-Induced Late Side Effects."

Bennett, MH, et al, Hyperbaric oxygen therapy for late radiation tissue injury (Review), Copyright 2009 The Cochrane Collaboration. Published by John Wiley & Sons, Ltd. Issue 2.

Mayer, R., et al, *Strahlenther Onkol*, No. 2, pp. 113-123 (2005), "Hyperbaric Oxygen and Radiotherapy."

Williamson, et al, *Int. J. Oral Maxillofac. Surg.*, 36, pp. 533-540, (2007), "An experimental study of the use of hyperbaric oxygen to reduce the side effects of radiation treatment for malignant disease."

Greenwood, T.W., et al, Brit. J. Surg., vol. 60, No. 5, May 1973, pp. 394-397, "Hyperbaric Oxygen and Wound Healing in Post-Irradiation Head and Neck Surgery."

Marx, R.E., et al, *The American Journal of Surgery*, vol. 160, pp. 519-524, Nov. 1990, "Relationship of Oxygen Dose to Angiogenesis Induction in Irradiated Tissue."

Gill, A.L., et al, Q J Med, 97, pp. 385-395, (2004), "Hyperbaric oxygen: its uses, mechanisms of action and outcomes."

Cianci, P, (*see Cianci, P., Hyperbaric therapy for radiation injury*, in "Radiation Injury, Advances in Management and Prevention" edited by J.L. Meyer, et al, pp. 98-109, (1999)).

Okonkwo, D.O., et al, *Neuroscience Letters*, 352, pp. 97-100, (2003), "Trans-sodium crocetinate increases oxygen delivery to brain parenchyma in rats on oxygen supplementation."

Giassi, L.J., et al, *Journal of Trauma*, 51, pp. 932-938, (2001), "Trans-Sodium Crocetinate Restores Blood Pressure, Heart Rate, and Plasma Lactate after Hemorrhagic Shock."

Gainer, J.L., et al, *Pulmonary Pharmacology & Therapeutics*, 18, pp. 213-216, (2005), "The effect of trans sodium crocetinate (TSC) in a rat oleic acid model of acute lung injury."

Huxley, V.H., et al, *J. Physiol.*, 316, pp. 75-83, (1981), "The Effect of the Red Cell Membrane and a Diffusion Boundary Layer on the Rate of Oxygen Uptake by Human Erythrocytes."

Yamaguchi, K., et al, *the American Physiological Society*, pp. 1215-1224, (1985), "Kinetics of O2 uptake and release studied by human erythrocytes studied by a stopped-flow technique."

Gainer, J.L., et al, *Circulatory Shock*, 41, pp. 1-7, (1993), "The Effect of Crocetin on Hemorrhagic Shock in Rats."

Roy, J.W., et al, *Shock*, vol. 10, No. 3, pp. 213-2171, (1998), "A Novel Fluid Resuscitation Therapy for Hemorrhagic Shock."

Singer, M., et al, *Crit Care Med*, vol. 28, No. 6, pp. 1968-1972, (2000), "Intravenous crocetinate prolongs survival in a rat model of lethal hypoxemia."

Giassi, L.J., et al, *Shock*, 18(6), pp. 585-588 (2002), "Trans Sodium Crocetinate for Hemorrhagic Shock: Effect of Time Delay in Initiating Therapy."

Ladig, K.E., et al, *Journal of the American Chemical Society*, vol. 120, No. 36, pp. 9394-9396, (1998), "Altering Diffusivity in Biological Solutions through Modification of Solution Structure and Dynamics."

Mexican Office Action dated May 2010, and English translation of rejected parts of the Office Action, from Mexican Patent Application No. PA/a/2004/008253 corresponding to International Patent Application No. PCT/EP2003/005521.

Notification Concerning Transmittal of International Preliminary Report on Patentability (Chapter 1 of the Patent Cooperation Treaty), dated May 14, 2010.

International Preliminary Report on Patentability, dated May 4, 2010.

Written Opinion dated Mar. 25, 2009 in PCT/US2008/012440 [previously submitted].

Korean Office Action dated May 26, 2009, and English translation in a corresponding application owned by the applicants.

Japanese Patent Office Action dated Jun. 2, 2009 and its English translation, cited in one of Assignee's Japanese patent applications.

Isler, O., et al, Helv. Chim. Acta., vol. 40, No. 5, 1957, pp. 1242-1249.

Examination Report dated Apr. 12, 2010 issued by the India Patent Office in one of Applicants' corresponding foreign applications.

Australian Office Action dated Mar. 26, 2010 in applicant's Australian application No. 2003265617.

Pfander, H. et al, *Pure & Appl. Chem.*, vol. 69, No. 10, pp. 2047-2060 (1997), "Carotenoid synthesis: A progress report."

Widmer, Erich et al, Helvetica Chemica Acta—vol. 73 (1990), pp. 861-867, Technical Procedures for the Syntheses of Carotenoids and Related Compounds . . . .

Norwegian Office Action and its English Translation mailed Jun. 22, 2010 in the Assignee's Norwegian application relating to PCT/US03/05521.

Database Caplus, Chemical Abstracts Service, Columbus, Ohio, US; XP002317165 [JP 63 059831].

Supplementary European Search Report dated Apr. 29, 2010 issued by the EPO in one of Applicants' corresponding foreign applications.

Schwieter, U., et al, "Synthesen in der Carotinoid-Reiche 20. Mitteilung Neu Synthesen von Apocarotinoiden," Helvetica Chimica Acta, vol. 1, (1966), pp. 369-390, XP-002575142.

Britton, G. et al, *Carotenoids*, vol. 1A, Birkhauser-Verlag, Basel, 1995, p. 7, 35.

Pauling, L., Fortschr. Chem. Org. Naturst., 3:303 (1939), p. 203-235.

Korean Office Action and its English Translation dated Jul. 6, 2010 in the Assignee's Korean application 10-2004-7013118, that is the nationalized appln. from PCT/US03/05521, claiming priority from U.S. Appl. No. 60/358,718.

Korean Office Action and its English Translation dated Jun. 22, 2010 from applicant's Korean Patent Appln. No. 10-2006-7003827, that corresponds to PCT/US03/26424.

Zheng, S., et al, "Crocetin Attenuates Atherosclerosis in Hyperlipidemic Rabbits Through Inhibition of LDL Oxidation," Journal of Cardiovascular Pharmacology, vol. 47, No. 1, Jan. 2006, pp. 70-76, XP009135396, ISSN: 0160-2446.

Examination Report dated Jul. 2, 2009 issued by the New Zealand Patent Office in one of Applicants' corresponding foreign applications.

Japanese Patent Office Action dated Jun. 2, 2009 and its English translation, cited in one of Assignee's Japanese patent applications (No. 2003-571422).

Wirz, R. et al, Helvetica Chimica Acta, 1960, 43(6), 1738-1745.

Wenkert, E. et al, Journal of Organic Chemistry, Dec. 7, 1990, Vo. 55, No. 25, pp. 6203-6214.

Ukraine Office Action issued Aug. 2010.

Written Opinion and International Search Report issued in PCT/US06/06422 dated Oct. 19, 2006.

International Search Report dated Sep. 1, 2010 in PCT/US 10/01794.

Written Opinion dated Sep. 1, 2010 in PCT/US 10/01794.

Canadian Office Action issued Jul. 7, 2010 in corresponding Canadian Application No. 2477245.

Wirz, R., et al, *Helv. Chim. Acta*, vol. 43(6), pp. 1738-1745, 1960, (XP008042762).

Wenkert, E., et al, *J. Org. Chem.*, vol. 55(25), pp. 6203-6214, 1990, (XP002317164).

RN: 33261-80-2; CN: 2,4,6,8,10,12,14,16,18-Eicosanonaenedioic acid, 4,8,13,17-tetramethyl-dipotassium salt.

RN: 33261-81-3; CN: 2,4,6,8,10,12,14,16,18-Eicosanonaenedioic acid, 4,8,13,17-tetramethyl-disodium salt.

RN: 120523-11-7; CN: 2,4,6,8,10,12,14,16,18-Eicosanonaenedioic acid, 4,8,13,17-tetramethyl-potassium sodium salt.

RN: 147484-59-1; CN: 2,4,6,8-Decatetraenedioic acid, disodium salt.

Polish Office Action dated Sep. 2010 in corresponding Polish Application No. P-373780.

Office Action dated Oct. 28, 2009 from Application U.S. Appl. No. 11/361,054.

International Preliminary Report on Patentability—issued Oct. 13, 2009 in PCT/US2008/004708.

Canadian Office Action dated Oct. 20, 2009 from Canadian Application No. 2,477,245.

Hungarian Novelty Search Report dated Nov. 5, 2009 (w/translation).

Canadian Office Action issued Oct. 26, 2010 in corresponding Canadian Application No. 2537210.

Examination Report dated Oct. 25, 2010 issued by the Australian Patent Office in one of Applicants' corresponding foreign applications.

Wilkins, E.S., et al, *Cancer Biochem. Biophys.*, 1979, vol. 3, pp. 71-74, "The Effect of Crocetin on the Irradiation of Walker-256: In Vitro and In Vivo Studies."
Office Action dated Dec. 4, 2008 from U.S. Appl. No. 11/361,054.
Chem. Abstr. of JP 05032531.
Office Action dated Nov. 13, 2008 from U.S. Appl. No. 10/647,132.
International Search Report dated Sep. 9, 2011 in PCT/US 11/00997.
Written Opinion dated Sep. 9, 2011 in PCT/US 11/00997.
Eurasian Patent Office Action (English translation) dated Nov. 9, 2011.
Japanese Notice of Reasons for Rejection and its English Translation dated May 24, 2011.
Office Action issued in Japanese Patent Appln. No. 2007-557157 and English translation (corresponding to PCT App. No. US 2006/006422) dated May 24, 2011.
Chinese Patent Office Action (English translation) dated Jun. 30, 2011.
Canadian Office Action dated Jul. 5, 2011.
Office Action dated Sep. 22, 2011 from U.S. Appl. No. 11/790,779.
Japanese Office Action mailed Oct. 4, 2011, and English translation.
Wirz, R., et al, Helv. Chim. Acta, vol. 43, No. 6, 1960, pp. 1738-1745, (XP008042762).
Wenkert, E., et al, J. Org. Chem., vol. 55, No. 25, 1990, pp. 6203-6214, (XP002317164).
Nihon Butsuri Gakkai Shi, *Journal of the Physical Society of Japan*, 1995, 50(7), p. 555-561, "Structure and Function of Cartenoid in Photosynthetic System."
EP Office Action dated Apr. 7, 2011, from European Patent Application No. EP 08742781.1.
Mexican Office Action dated Oct. 20, 2011 (with English translation).
Johnson, et al, *Journal of Pharmaceutical Sciences*, vol. 85, No. 7, 1996, pp. 670-679, "Synergistic effects of chemical enhancers and therapeutic ultrasound on transdermal drug delivery."
Norway Office Action dated Feb. 16, 2011, from Norway Patent Application No. 20043661, and its English translation.
Wirz, R., et al, Helv. Chim. Acta, vol. 43, No. 6, 1960, pp. 1738-1745.
Database Caplus (Chem. Abs. Service, USA) acc. Nr. 1989:211328.
Isler, O., et al, Helv. Chim. Acta, vol. 40, No. 5, 1957, pp. 1242-1249.
Japanese Office Action and its English Translation dated Apr. 6, 2010 in the Assignee's Japanese application relating to PCT/US2006/006422.
Examination Report dated Oct. 7, 2010 issued by the New Zealand Patent Office in one of Applicants' corresponding foreign applications.
IPRP issued in corresponding PCT Appln. No. PCT/US2008/004708.
Office Action dated Jan. 4, 2012 from U.S. Appl. No. 13/137,337.
European Patent Office Action dated Oct. 31, 2011, from European Patent Application No. EP 06758166.0.
Office Action dated Dec. 19, 2011 from U.S. Appl. No. 12/801,726.

\* cited by examiner

CLASS OF THERAPEUTICS THAT ENHANCE SMALL MOLECULE DIFFUSION

This application claims priority from U.S. Provisional Patent Application No. 61/001,095, filed Oct. 31, 2007, the entire contents of which are hereby incorporated by reference.

The subject application relates to novel compositions and their use in enhancing small molecule diffusion, and in the case of oxygen in vivo, oxygenation of tissues. This class of compounds is called diffusion enhancing compounds.

BACKGROUND OF THE INVENTION

The terms 'kosmotrope' (order-maker) and 'chaotrope' (disorder-maker) originally denoted solutes that stabilized, or destabilized respectively, proteins and membranes. More recently, the terms have also been used to refer to compounds having the apparently correlating property of increasing, or decreasing respectively, the structuring (ordering) of water. Some compounds (e.g. urea) can act as kosmotropes and chaotropes, depending on the concentration of the compound in a hydrogen bonding environment such as water.

Both the extent and strength of hydrogen bonding may be changed by a kosmotrope. The effect of a kosmotrope on increasing the amount of hydrogen bonding in an aqueous solution is especially important. By effecting such a change in the hydrogen bonding in the solution, a kosmotrope shifts the local equilibrium shown below to the left (and chaotropes shift it to the right)

less dense water $\rightleftharpoons$ more dense water.

In other words, the addition of a kosmotrope to an aqueous system results in a decrease in density of that system. So, by increasing the structure, or order, of the water through the formation of more hydrogen bonds, kosmotropes cause the solution density to decrease.

Kosmotropes are currently used to stabilize proteins, such as enzymes. It is also said that they affect the phase behavior of lipids. Some well-known kosmotropes are proline, glycine betaine and trehalose. See also Moelbert, S. et al., Biophysical Chemistry, 112, 45-57, 2004. The website: http://www.lsbu.ac.uk is a good reference for kosmotropes and chaotropes.

Gainer et al. *Chem. Eng. Commun.* 15: 323-329, 1982, showed that crocetin caused an increase in the specific volume of water.

Gainer et al. *Ind. Engr. Chem. Research*, 33: 2341-2344, 1994 showed that the diffusivity through a solution was proportional to the change in the specific volume.

Carotenoids are a class of hydrocarbons consisting of isoprenoid units. The backbone of the molecule consists of conjugated carbon-carbon double and single bonds, and can also have pendant groups. Carotenoids such as crocetin and trans sodium crocetinate (TSC) are known to increase the diffusivity of oxygen in water.

U.S. Pat. No. 6,060,511 relates to trans sodium crocetinate (TSC) and its uses. The patent covers various uses of TSC such as improving oxygen diffusivity and treatment of hemorrhagic shock.

U.S. patent application Ser. No. 10/647,132 relates to synthesis methods for making bipolar trans carotenoid salts (BTC) and methods of using them.

U.S. patent application Ser. No. 11/361,054 relates to improved BTC synthesis methods and novel uses of the BTC.

U.S. Patent Application Ser. No. 60/907,718 relates to the use of bipolar trans carotenoids as a pretreatment and in the treatment of peripheral vascular disease.

Trans sodium crocetinate (TSC) increases the amount of hydrogen bonding when dissolved in water, Stennett et al. J. Phys. Chem. B, 110: 18078-18080, 2006.

In Okonkwo et al., Neurosci Lett. 352(2):97-100, 2003, the authors measured brain oxygen levels in rats. As expected, having the rats breathe 100% oxygen caused the brain oxygen level to increase. An unexpected result was that administering TSC to rats breathing 100% oxygen further increased the brain oxygen level. The combination of 100% oxygen and TSC gave a greater effect than either one alone. In animals suffering from an oxygen deficiency, TSC can be used as a treatment, Giassi, L. J. et al. *J. Trauma*, 51: 932-938, 2001, and Gainer et al. *Pulm. Pharmacol. &Therapeutics*, 18: 213-216 (2005).

SUMMARY OF THE INVENTION

The subject invention relates to pharmaceutical compositions comprising a diffusion enhancing compound such as a kosmotrope, and a pharmaceutically acceptable carrier.

The invention also relates to a variety of methods of treatment including methods of enhancing the diffusion of oxygen, treating hemorrhagic shock, or treating a hypoxic condition in a mammal comprising administering to said mammal a therapeutically effective amount of a diffusion enhancing compound other than a bipolar trans carotenoid.

The invention also relates to a method of treating cancer comprising administering to said mammal a therapeutically effective amount of a diffusion enhancing compound as an adjunct to radiation therapy and/or chemotherapy.

The invention also relates to treating diseases where organs do not get enough oxygen such as Wegener's granulomatosis with a diffusion enhancing compound including bipolar trans carotenoids, and to treating arthritis with a diffusion enhancing compound including a bipolar trans carotenoid other than crocetin.

DETAILED DESCRIPTION OF THE INVENTION

Figure 1:
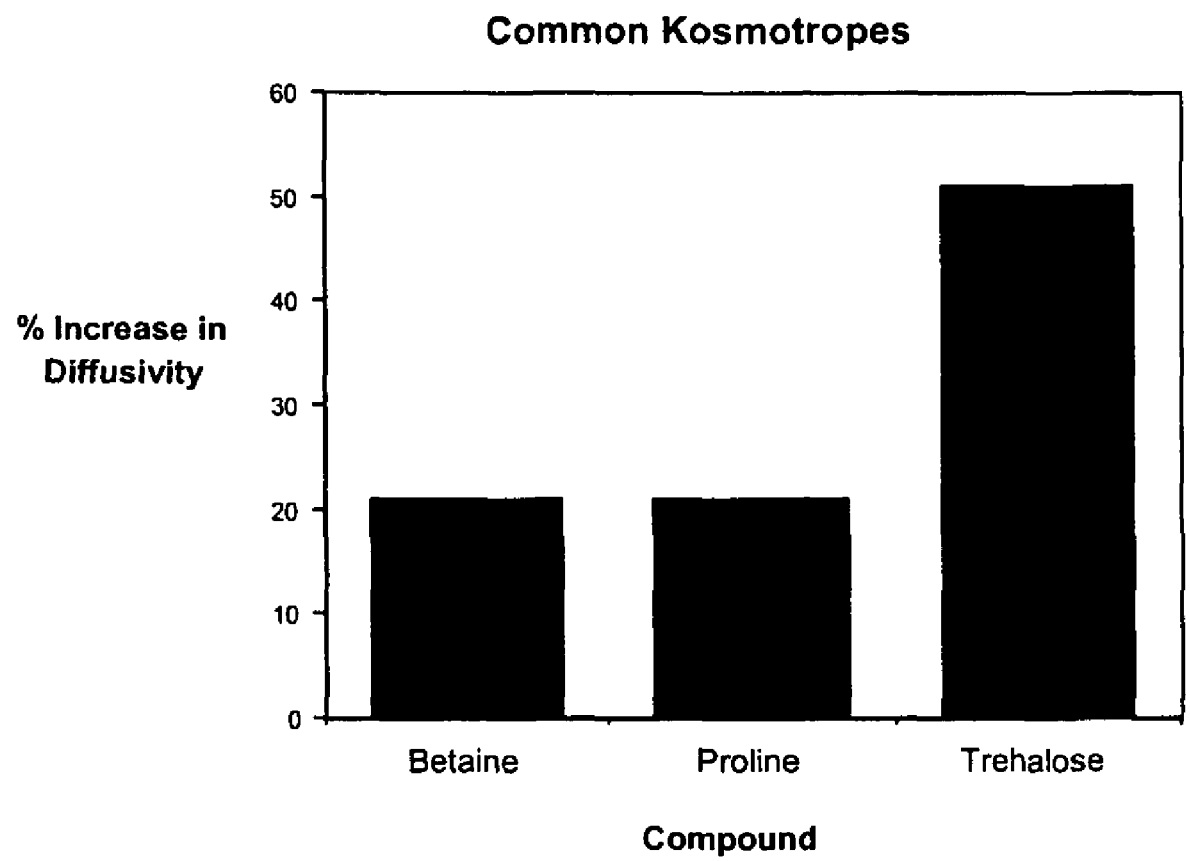
FIG. 1 is a graph of percentage increases in the diffusivities of glucose due to each kosmotrope.

The subject invention relates to novel compositions and their use in treating a variety of disorders where enhanced tissue oxygenation is beneficial. As used herein, "diffusion enhancing compound" is a compound that causes an increase in the rate of movement of a small molecule through an aqueous system. Diffusion enhancing compounds increase the specific volume of the aqueous system by increasing water structure by affecting the extent and strength of hydrogen bonding among water molecules.

The movement of oxygen through plasma is thought to be a limiting, or controlling, step in the uptake and release of oxygen from red blood cells (Holland, RAB, Shibata, H., Scheid, P, Piiper, J: *Respiration Physiology*, 59: 71-91, 1988; Huxley, V H, Kutchai, H: *J. Physiology*, 316: 75-83, 1981; Yamaguchi, K, Nguyen-Phu, P. Scheid, P, Piiper, J: J. Applied Physiology, 58: 1215-1224, 1985). Thus, in order to increase the rate at which oxygen gets to the body tissues, it is important to enhance its movement through the plasma.

Oxygen can move through the plasma, especially in the smaller blood vessels (the capillaries), via molecular diffusion which depends on the oxygen concentration gradient as well as a factor called the diffusion coefficient (or diffusivity). This diffusion coefficient reflects the basic resistance of the plasma to the movement of other molecules like oxygen, through it. If it were possible to decrease the resistance of the plasma, oxygen would move faster through it and this would be reflected as an increased diffusivity. One way to do this is to decrease the plasma density with a diffusion enhancing compound.

Usually when one adds a chemical compound to a given volume of plasma, the density (mass/volume) increases. Thus, in order to decrease the density of plasma when adding another substance, the compound added must also increase the volume of the liquid as well as the mass of the solution. This will result in a decrease in the density (mass/volume). Specific volume is inversely related to the density. Increasing the specific volume (volume/mass) of the blood plasma implies altering the "structure" of its water molecules.

Compounds that decrease the water density and increase the specific volume are kosmotropes. Kosmotropes are said to shift the equilibrium shown below to the left while compounds called chaotropes shift it to the right:

less dense water ⇌ more dense water

Thus, kosmotropes are diffusion enhancing compounds. How they act to decrease water density has been suggested to be through increasing the water structure through increased hydrogen bonding. Plasma is mostly water and water molecules are bound to each other by hydrogen bonds.

The terms 'kosmotrope' (order-maker) and 'chaotrope' (disorder-maker) also denote solutes that stabilized, or destabilized respectively, proteins and membranes. Another term used to classify compounds and ions which stabilize proteins in cells is osmolyte. A number of chemical compounds are included on both the lists of osmolytes and the lists of kosmotropes. Osmolytes are frequently concentrated inside tissue cells.

As used herein "diffusion enhancing kosmotrope" denotes kosmotropes having the capability to increase the structuring (ordering) of water, resulting in a decreased density and an increased diffusivity of oxygen through an aqueous solution like plasma.

Both the extent and strength of hydrogen bonding can be changed by a kosmotrope. Some compounds (e.g. urea) can act as both a kosmotrope and a chaotrope, depending on the concentration of the compound in a hydrogen bonding environment such as water. Some of the better-known kosmotropes are proline, glycine betaine and trehalose.

As shown in the Examples below, it can be seen that kosmotropes increase the diffusivity of solutes (such as glucose and oxygen) through aqueous solutions. They do this because kosmotropes cause increased hydrogen bonding among the water molecules, which, in turn, leads to a less dense liquid structure.

Also included in diffusion enhancing compounds are the bipolar trans carotenoid compounds. Carotenoids are not found on standard lists of kosmotropes; however, it has been found that a carotenoid, trans sodium crocetinate (TSC), can enhance water structure (Laidig, K. E., Gainer, J. L., Daggett, Valerie: *Journal of the American Chemical Society,* 120: 9394-9395, 1998) as well as cause increased hydrogen-bonding in water (Stennett, A. K., Dempsey, G. L., Gainer, J. L.: J. of Physical Chem. B, 110: 18078-18080, 2006). Trans sodium crocetinate is also known to increase the diffusivity of both oxygen and glucose (Stennett, A. K., Dempsey, G. L., Gainer, J. L.: J. of Physical Chem. B, 110: 18078-18080, 2006).

Thus, diffusion enhancing compounds can cause increased water structure and decreased density, resulting in increased diffusivity through aqueous solutions such as blood plasma. These properties enable these compounds to perform as therapeutics to increase tissue oxygenation.

Other diffusion enhancing compounds increase the diffusion through aqueous solutions through the same mechanism, i.e., by decreasing the density and altering the water structure by increasing the hydrogen bonding among the water molecules. There are accepted methods of determining whether or not a compound increases the hydrogen bonding of water (Stennett et al., J. Phys. Chem. B., 110, 18078-18080, 2006).

Diffusion enhancing compounds will increase tissue oxygenation in a mammal. If the mammal is oxygen-deficient, or hypoxic, then no enriched oxygen gases are needed to observe the effect of a diffusion enhancing compound. If the mammal is not suffering from a form of hypoxia, then enriched oxygen gases plus a diffusion enhancing compound will deliver more oxygen to the tissue than the enriched oxygen gases can do alone.

Compounds and Compositions of the Invention

Included in the Compounds of the Invention are the following diffusion enhancing compounds:

Bipolar Trans Carotenoids such as trans sodium crocetinate (TSC). See also the compounds disclosed in U.S. Ser. No. 10/647,132 and U.S. Ser. No. 11/361,054 hereby incorporated by reference in their entirety Kosmotropes are effective in enhancing diffusion. As used herein, the term "kosmotrope" means a chemical compound that results in increased water structure by increasing hydrogen bonding among water molecules. Another characteristic of the kosmotropes of the invention are non toxic at therapeutically effective concentrations. Kosmotropes of the invention include:

Trimethylamine N-oxide

Proline

Ectoine

Trehalose, maltose and other disaccharides that can increase hydrogen bonding

Glycine betaine

3-Dimethylsulfoniopropionate

Urea at certain concentrations [it can be the opposite (a chaotrope) at other concentrations]

Maltose

Glycerol

Small or multiply-charged ions, with high charge density (e.g. $SO_4^{2-}$, $HPO_4^{2-}$, $Mg^{2+}$, $Ca^{2+}$, $Li^+$, $Na^+$, $OH^-$, $F^-$, $Cl^-$)

t-butanol

Fructose

DMSO (dimethylsulfoxide) at certain concentrations (it is like urea in that it is a chaotrope at other concentrations)

and other related compounds which also function as kosmotropes.

Other compounds that enhance the diffusion of oxygen in an aqueous system are also useful. In addition to the compounds above, the skilled person can use assays as described herein and known to those skilled in the art, to identify diffusion enhancing compounds that increase the specific volume of an aqueous system by increasing water structure by affecting the extent and strength of hydrogen bonding among water molecules.

The compounds of the subject invention are all manufactured to be pharmaceutical grade. Although the compounds of the invention can be administered alone, they can also be administered as part of a pharmaceutical composition. Such formulations can include pharmaceutically acceptable carriers known to those skilled in the art as well as other therapeutic agents—see below. Advantageously, the formulation does not include a compound that inhibits the ability of the compounds of the invention to improve diffusivity.

The compounds can be formulated using agents known to increase solubility such as cyclodextrins, polyethylene glycol, glycols, etc. Other agents can be added to buffer the diffusion enhancing compounds. Other agents can be added to affect the osmolality, as well as compounding agents needed for oral formulations.

The formulations can conveniently be presented in unit dosage form, e.g., tablets and sustained release capsules, and can be prepared and administered by methods known in the art of pharmacy. The formulation can be for immediate, or slow or controlled release of the diffusion enhancing compound. See, for example, the controlled release formulation of WO 99/15150 hereby incorporated by reference in its entirety.

Formulations of the present invention suitable for oral administration can be presented as discrete units such as pills, capsules, cachets or tablets, as powder or granules, or as a solution, suspension or emulsion. Formulations suitable for oral administration further include lozenges, pastilles, and inhalation mists administered in a suitable base or liquid carrier. Formulations for topical administration to the skin can be presented as ointments, creams, gels, and pastes comprising the active agent and a pharmaceutically acceptable carrier or in a transdermal patch.

Formulations suitable for nasal administration wherein the carrier is a solid include powders of a particular size that can be administered by rapid inhalation through the nasal passage. Suitable formulations wherein the carrier is a liquid can be administered, for example as a nasal spray or drops.

Formulations suitable for parenteral administration include aqueous and non-aqueous sterile injection solutions that can contain antioxidants, buffers, bacteriostats, compounds to improve solubility of the active agent, solutes which render the formulation isotonic with the blood of the intended recipient, and aqueous and nonaqueous sterile suspensions which can include suspending agents and thickening agents.

The formulations can be presented in unit or multi-dose containers, for example sealed ampules and vials, and can be lyophilized or crystallized, requiring only the addition of the sterile liquid carrier such as water for injection immediately prior to use. Injection solutions and suspensions can be prepared from sterile powders, granules and tablets.

Therapeutic Uses and Modes of Administration of the Compounds and Compositions of the Invention The compounds and compositions of the invention have therapeutic uses in treating mammals having conditions of reduced oxygen usage.

The uses include those disclosed in commonly owned U.S. Pat. No. 6,060,511, U.S. patent application Ser. No. 10/647,132, U.S. patent application Ser. No. 11/361,054, and U.S. Patent application Ser. No. 60/907,718 each of which is hereby incorporated by reference in its entirety. The compounds are useful in the treatment of:

hemorrhagic shock, respiratory disease, asthma, emphysema, ALI, ARDS, COPD cardiovascular disease, atherosclerosis, myocardial infarction, hypertension, ischemia, stroke, traumatic brain injury, Alzheimer's disease, arthritis, anemia, (anemia of prematurity, Fanconi anemia, hymolytic anemia, microcytic anemia, a normochromic anemia, a macrocytic anemia, hereditary spherocytosis, sickle-cell anemia, warm autoimmune hemolytic anemia, cold agglutinin hemolytic anemia), chronic renal failure, hypertension, cerebral edema, papillomas, spinal chord injuries cancer (advantageously as an adjunct to i) radiation therapy including external beam radiation, gamma knife, brachytherapy, tomotherapy, and proton beam, including fractionated, 3D conformal radiotherapy, intracavitary radiation, and intensity modulated radiotherapy (IMRT), and/or ii) chemotherapy including temozolimide), diabetes, diabetic retinopathy, peripheral vascular disease/claudication, embolism, blood clot, spinal stenosis/neurogenic claudication, diseases where organs do not get enough oxygen such as Wegener's granulomatosis performance when respiration/exertion is increased/stressed, The compounds and compositions of the invention are also useful as a pretreatment or for treating mammals at risk for the above-noted diseases/conditions.

As evidenced by the Examples below, diffusion enhancing compounds increase tissue oxygenation and thus can be used to treat oxygen deficient diseases. The concentration/dose of the diffusion enhancing compound selected will be that concentration that causes increased hydrogen bonding among the water molecules of the blood plasma and results in increased diffusivity. This concentration can be determined by those skilled in the art.

Typically the diffusion enhancing compounds are administered by any suitable route including oral, nasal or inhalation, topical, parenteral (including subcutaneous, intramuscular, intravenous, intradermal, transdermal and intraosseus), vaginal or rectal. The preferred route of administration will depend on the circumstances. An inhalation route is advantageous for treatment in emergency situations, where it is necessary for the diffusion enhancing compound to enter the bloodstream very quickly. The formulations thus include those suitable for administration through such routes (liquid or powder to be nebulized). It will be appreciated that the preferred route may vary, for example, with the condition and age of the patient.

Appropriate dosages of the compounds and compositions of the invention as well as the mode of administration, will depend on the metabolism of the given compound, and the severity of the condition being treated. For a dose to be "therapeutically effective", it must have the desired effect, i.e. increase diffusivity. The minimum dosage needed for treatment for any of these diffusion enhancing compounds is that at which the diffusivity increases. The therapeutically effective dosage of the compounds of the invention will depend upon the condition treated, the severity of the condition, the stage and individual characteristics of each mammalian patient addressed, and the clearance of the diffusion enhancing effect.

In one embodiment, more than one diffusion enhancing compound is administered. In another embodiment, the diffusion enhancing compound is administered along with oxygen. Alternatively, hemoglobins or fluorocarbons and a diffusion enhancing compound can be given together. In a still further embodiment, the diffusion enhancing compound is administered along with an erythropoiesis stimulating compound such as erythropoietin.

In another embodiment, diffusion enhancing compound can be used to increase the diffusivity of other physiologically important molecules other than oxygen such as glucose, CO2, or NO.

Non-Therapeutic Uses

Lastly, the compounds of the invention can be used to enhance diffusivity in aqueous systems outside the body, for example in fermentations and other cultures of microorganisms.

The following examples are illustrative, but not limiting of the compounds, compositions and methods of the present invention. Other suitable modifications, and adaptations of a variety of conditions and parameters normally encountered which are obvious to those skilled in the art are within the spirit and scope of the invention.

EXAMPLES

Example 1

Increasing Glucose and Oxygen Transport In Vitro

The effect of each of 3 kosmotropes (proline, betaine and trehalose) on the rate of diffusion though a water solution has been tested in the following manner.

Glucose Diffusion

The diffusion of glucose through aqueous solutions of the above-mentioned kosmotropes was measured using a micro-interferometric method, Secor, R. M., *AIChE Journal,* 11: 452-456, 1965.

In this method, a wedge is formed by two microscope slides that have a partial coating of a metal such as aluminum on the inner sides of the wedge. The wedge is placed on a microscope stage and illuminated from below using some source of monochromatic light, such as a helium-neon laser. As the light passes through the wedge, the partial coating of aluminum allows some light to be transmitted, while some is reflected. This creates constructive and destructive lines known as interference fringes. The interference fringes can then be magnified by a microscope and recorded with a camera.

Molecules of glucose will diffuse along a concentration gradient of glucose. Since the refractive index of the solution is related to the concentration of the glucose, the fringes at a given point will change with time. From the time behavior in the fringe pattern, one can calculate the diffusion coefficient, or diffusivity, at each time increment. These values become constant at longer times, and that final value is taken to be the diffusion coefficient of glucose in that particular aqueous solution.

Solutions of three kosmotropes (proline, betaine and trehalose) in water were made, so that the solutions contained about 10 µM of each of the kosmotropes. Using the trehalose solution as an example, the diffusivity of glucose through each of these solutions was then measured in the following way.

The trehalose solution was divided into two parts. A strip of one part of the trehalose solution was placed on one of the coated slides. A wedge was formed by placing a cover slip on one end of one of the coated slides and then resting the other coated slide on top. The wedge was placed on a microscope stage and a light source was turned on. A camera recorded the resulting fringe pattern.

Glucose was added to the second portion of the trehalose solution so that the glucose concentration in that solution was 0.9 molar. A drop of this trehalose-glucose solution was then introduced into the wedge, using a syringe, in such a manner so that the drop touched the strip of trehalose solution that was already in the wedge. Care was taken to assure that the two solutions did not mix when they touched, and, if they did, the solution was discarded and the procedure started over.

A stopwatch was turned on at the time that the two solutions touched. Pictures of the fringe patterns were taken at various times over the next several minutes. Using these pictures, it is possible to calculate the diffusivity of glucose through the trehalose solution. That calculation method is given in Secor, R. M., *AIChE Journal,* 11: 452-456, 1965.

The measurements were done at a temperature of 25° C., and the apparatus was calibrated by measuring the diffusivity of glucose in plain distilled water, with the value obtained being $(6.9\pm0.3)\times10^{-6}$ cm$^2$/s. This closely corresponds to the CRC Handbook value of $6.7\times10^{-6}$ cm$^2$/s CRC Handbook of Chemistry and Physics, edited by D. R. Lide, CRC Press, Boca Raton, Fla., 1998, p. 6-181.

The values of the diffusivity of glucose through the solutions containing the trehalose and the other kosmotropes were greater than the value of glucose through plain water. The percentage increases in the diffusivities of glucose due to each kosmotrope is shown in FIG. 1.

The preceding diffusion measurement was also done for TSC in water, and it was found that TSC caused an increase in the diffusivity of glucose through water at TSC concentrations from 1 µmole/liter to around 200 µmole/liter of around 30%, Stennett, A. et al. J. Phys. Chem. B, 110: 18078-18080, 2006.

Oxygen Diffusion

In addition, the diffusivity of oxygen through TSC-water solutions was also measured over the same TSC concentration range as for the glucose diffusion studies. Since oxygen is a gas, the diffusivity had to be measured differently, in an apparatus commonly used for such purposes, Goldstick, T. K., PhD Dissertation, University of California, Berkeley, Calif., 1966, pps. 13-28. In that experiment, the movement of oxygen across a liquid layer is determined by measuring the concentration at the opposite boundary of the liquid layer over time using an electrode, and the diffusivity calculated. All measurements were done at 25° C., and it was found that TSC increases the diffusion of both oxygen and glucose through water by a similar percentage, Stennett, A. K. et al. J. Phys. Chem. B, 110: 18078-18080, 2006.

Based on these data, it can be seen that kosmotropes increase the diffusivity of solutes (such as glucose and oxygen) through aqueous solutions.

Example 2

Increasing Oxygen Transport In Vivo

Diffusion enhancing compounds such as kosmotropes increase the oxygen transport in vivo. In the subject experiment, the oxygen diffusing through the skin of a normal, non-diseased rat was measured using a transcutaneous oxygen monitor (TCOM). In the subject study, the rats breathed air and then were switched to breathing 100% oxygen at a time equal to zero. Also at time zero, the rats were injected (intravenously in the femoral vein) with either saline (control), trehalose, glycine betaine, or TSC.

Figure 2:
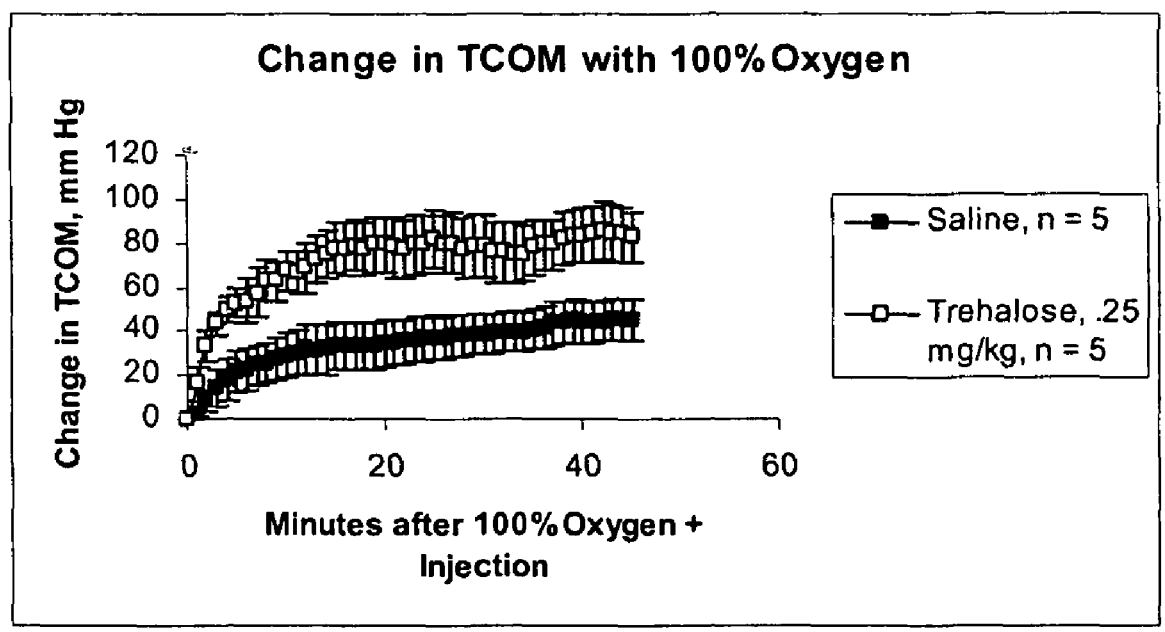
FIG. 2 is a graph that shows trehalose results in an increased oxygen transport across the skin.
Figure 3:
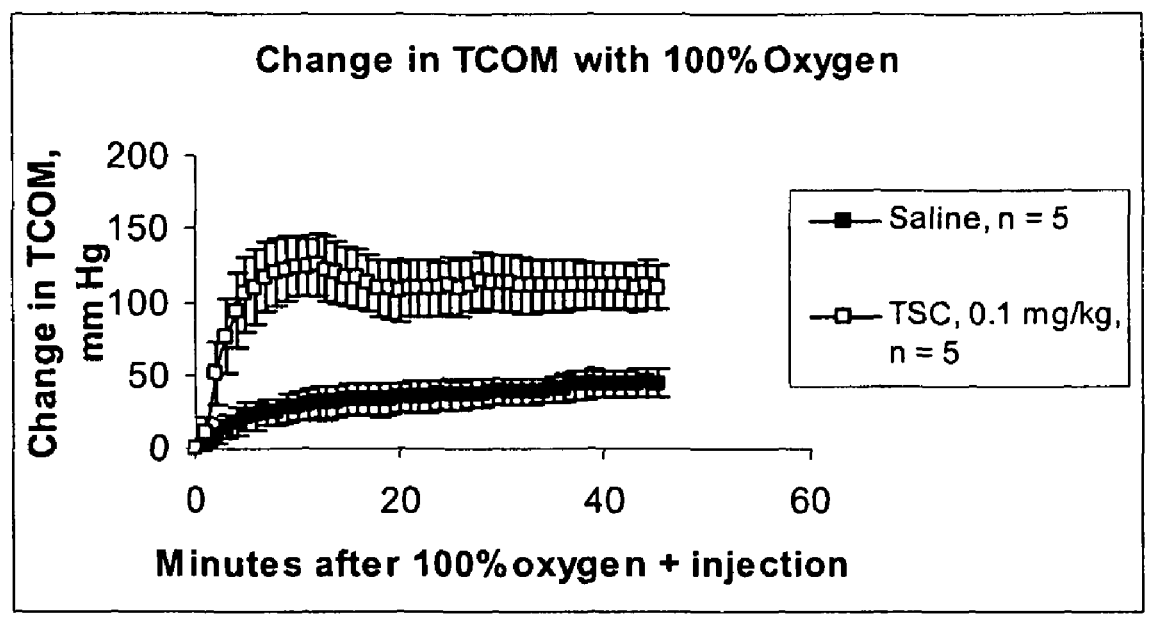
FIG. 3 is a graph that shows TSC results in an increased oxygen transport across the skin.
Figure 4:
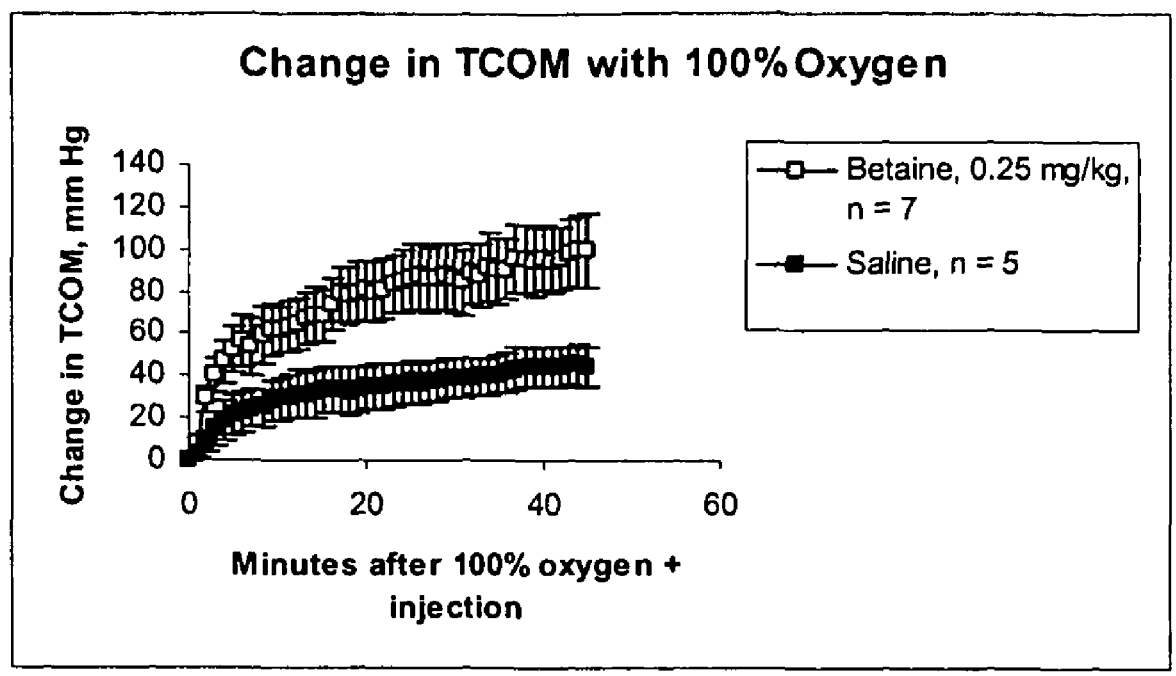
FIG. 4 is a graph that shows glycine betaine results in an increased oxygen transport across the skin.

FIGS. 2-4 show that trehalose, TSC, or glycine betaine result in an increased oxygen transport across the skin. All of these compounds increase the TCOM readings, as shown below by the average increases (±standard error). Thus, TSC, betaine and trehalose increase oxygen transport in vivo.

It will be readily apparent to those skilled in the art that numerous modifications and additions can be made to both the present compounds and compositions, and the related methods without departing from the invention disclosed.

What is claimed is:

1. A method of enhancing the diffusion of oxygen in a mammal comprising administering a diffusion enhancing compound other than a bipolar trans carotenoid in an amount sufficient to increase the diffusion of oxygen in blood plasma by increasing hydrogen bonding among water molecules in the blood plasma, and wherein the diffusion enhancing compound is selected from the group consisting of trimethylamine N-oxide, proline, ectoine, maltose, trehalose and other disaccharides which cause increased hydrogen bonding in blood plasma, glycine betaine, 3-dimethylsulfoniopropionate, urea, glycerol, small or multiply-charged ions with high charge density selected from the group consisting of $SO_4^{2-}$, $HPO_4^{2-}$, $Mg^{2+}$, $Ca^{2+}$, $Li^+$, $Na^+$, $OH^-$, $F^-$, and $Cl^-$, t-butanol, and DMSO (dimethylsulfoxide).

2. A method as in claim 1, wherein the diffusion enhancing compound is selected from the group consisting of trehalose, glycine betaine, and proline.

3. A method as in claim 1, wherein said administration is selected from the group consisting of nasal, parenteral, transdermal, intramuscular injection and oral delivery.

* * * * *